United States Statutory Invention Registration [19]

Fertel et al.

[11] Reg. Number: H992

[43] Published: Nov. 5, 1991

[54] PREPARATION OF FLUOROBENZENES BY THE DECARBOXYLATION OF FLUOROPHTHALIC ACIDS OR BENZOIC ACIDS

[75] Inventors: Lawrence B. Fertel, Buffalo; Henry C. Lin, Grand Island, both of N.Y.

[73] Assignee: Occidental Chemical Corporation, Dallas, Tex.

[21] Appl. No.: 574,861

[22] Filed: Aug. 30, 1990

[51] Int. Cl.[5] ..... C07C 17/33; C07C 17/22; C07C 22/08

[52] U.S. Cl. ..... 570/142

[58] Field of Search ..... 570/142

[56] References Cited

U.S. PATENT DOCUMENTS 4,782,180 11/1988 Wemple et al. ..... 562/479

FOREIGN PATENT DOCUMENTS 61-43130 3/1986 Japan .
43130 3/1986 Japan ..... 570/142
61-103317 3/1986 Japan .
61-85349 4/1986 Japan .
63-295529 12/1988 Japan .
64-25737 1/1989 Japan .
64-52737 2/1989 Japan .
2122190 1/1984 United Kingdom ..... 570/142

OTHER PUBLICATIONS

Yakobson, O. J., JH. Obsch. Khim 36 (1966), pp. 139 (in J. Gen. Chem. USSR, translated from Russian), 36 (1966), pp. 144.

*Primary Examiner*—Robert L. Stoll
*Assistant Examiner*—Joseph D. Anthony
*Attorney, Agent, or Firm*—James F. Tao; John H. Engelmann

[57] ABSTRACT

Polyfluorobenzenes are prepared by the decarboxylation of polyfluorophthalic acids or polyfluorobenzoic acids, in the presence of a Cu, CuO or $Cu_2O$ catalyst in either quinoline or N-methyl-2-pyrrolidone as a solvent.

14 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PREPARATION OF FLUOROBENZENES BY THE DECARBOXYLATION OF FLUOROPHTHALIC ACIDS OR BENZOIC ACIDS

BACKGROUND OF THE INVENTION

This invention relates to a method for the preparation of di, tri, and tetra fluorobenzenes as well as di, and trifluorochlorobenzenes by decarboxylation of the corresponding phthalic or benzoic acid. Such substituted benzenes have been prepared by several methods. For example, 1,2,3,4-tetrafluorobezene has been prepared by a number of methods. Banks, et. al. disclose a reaction in which 1,2,3,4,7,7-hexafluorobicyclo [2,2,1]hepta-2,5-diene rearranges to 1,2,3,4-tetrafluorobenzene upon being heated to 450° C. (J. Fluor. Chem., 26 (1984) 169) the yield is reported to be 74%. Japanese Patent No. JP61047426 (1986) (as abstracted in Chem, Abs. 105:114709E) discloses a method for fluorination of 1,2,3,4-tetrachlorobenzene with a mixture of KF/CsF in benzonitrile at 350° C. 1,2,3,4 tetrafluorobenzene is produced in 24.7% yield accompanied by partially fluorinated materials.

Finger et.al. report (J. Fluor. Chem. 2(1), 19 (1972) 1,2,4-trifluorobenzene may be prepared in 34% yield by the fluorination of 1,2,3,trichlorobenzene. Zweig, et. al. disclose (J. Org. Chem. 45, 3597 (1980) that 1-chloro-3,4-difluorobenzene may be prepared in 5.4% yield by treating 1,4-difluorobenzene with silver fluoride. The authors also obtained 1,2,4-trifluorobenzene in a 3% yield by an analogous reaction starting from 1,2-difluorobenzene. The polyfluorobenzenes and the fluoro-chlorobenzenes which are produced by the process of this invention have found uses as intermediates in a variety of pharmaceutical and agricultural applications. For example, 1,2,4 trifluorobenzene is a useful intermediate in the production of quinolone antibacterials. 1-chloro-3,4 difluorobenzene can be used to make quinolone antibacterials as well. In addition, the polyfluorobenzenes may be nitrated, and subsequently reduced to form fluorinated anilines which have found wide uses as pharmaceutical intermediates.

Many examples of decarboxylation reactions have been reported. Basic substances have been used to catalyze such reactions. For example, it is disclosed in D. S. Tarbell, et al Org. Syn., Coll. Vol. III (1955) 267, that 3,5-dichloro-4-hydroxybenzoic acid may be decarboxylated by vigorous heating in N,N-dimethylaniline. It is disclosed in A. Singer and S. M. McElvane, Org. Syn., Coll. Vol. II (1943) 214, that 3,5-dicarboxy-2,6-dimethylpyridine di-potassium salt may be completely decarboxylated by heating the salt in the presence of calcium hydroxide. Copper and copper salts have been used to catalyze decarboxylation reactions. For example, H. R. Snyder et al, Org. Syn., Coll. Vol. III (1955) 471 disclose the use of a copper oxide catalyst for the decarboxylation of imidazole 4,5-dicarboxylic acid.

Some compounds may be decarboxylated without catalysts. For example, C. Wang, Bul. Inst. Kim. Acad. Sinica, no. 2156 (1972), as abstracted in Chem. Abstracts (CA79 (15):91729), discloses that tetrachloro or tetrabromophthalic acids, or their anhydrides, may be decarboxylated to the corresponding benzoic acids when refluxed in dimethyl formamide. 3-Nitrophthalic acid underwent a similar reaction.

Decarboxylation is not always a predictable reaction. For example, A. S. Sultanov, J. Gen. Chem. (USSR) 16 1835 (1946) as abstracted in CA 41:6223(e) discloses that salicylic acid may be decarboxylated by autoclaving the acid in the presence of copper bronze and benzene at 170° C. The acid alone decarboxylates at 205° C., while in the presence of aniline decarboxylation begins at 170° C. In the case of salicylic acid, aniline and copper bronze seem to be equal in catalytic ability. On the other hand, when phthalic acid is heated in aniline at 180° C., decarboxylation does not occur and instead phthalic anhydride is produced. Heating phthalic anhydride with copper bronze in chloroform at 180° C. gave a 22% yield of benzoic acid. Phthalic acid was found to decarboxylate to yield benzoic acid merely by heating in water at 235° C.

Decarboxylations of certain fluorophthalic acids have been reported. 3,4,5,6-tetrafluorophthalic acid decarboxylates under certain conditions to yield 2,3,4,5-tetrafluorobenzoic acid. For example, Japanese Patent JP 61/85349 A2[86/85349]as abstracted in Chem. Abstracts (CA105:152719r), discloses that the reaction may be conducted in an aqueous medium at 150 to 230° C. The reaction may be carried out at a lower temperature (100° to 250° C.) in the presence of copper, zinc, cadmium, iron, cobalt, nickel, other oxides, hydroxides and/or carbonates. Japanese Patent Application 86/103,317 as abstracted in Chem. Abstracts (CA105 (22):193368u), discloses that the above reaction may be conducted in an aqueous medium at a pH of 0.7–2.2 at a temperature of 100°–200° C. The pH of the medium is adjusted by acidifying with sulfuric acid and partial neutralization with calcium hydroxide. Japanese Patent 63/295529m A2[88/295529]as abstracted in Chem. Abstracts (CA 111 (3): 23221X), discloses that the reaction may be conducted at 130 in tri-butylamine.

Yacobsen, O. J. discloses in Zh. Obsch. Khim. 36 (1966) page 139 (as appearing in Journal of General Chemistry of the U.S.S.R. translated from Russian 36 (1966) page 144), that 2,3,4,5-tetrafluorophthalic acid may be decarboxylated to yield 2,3,4,5-tetrafluorobenzoic acid by heating for one hour at 145° C. in dimethyl formamide solvent. See in addition United Kingdom Patent 2,122,190 (Inventors: David John Milner and Jerzy Czyzewski).

Japanese Patent JP 01/52737 as abstracted in Chem. Abstract (CA)111 (14):117305e discloses the preparation of 2,4,5-trifluorobenzoic acid by the decarboxylation of 3,4,6-trifluorophthalic acid in a liquid medium at a temperature of 80°–250° C.

Under slightly more vigorous conditions, Japanese Patent Application 61/43130 A2[86/43130]as abstracted in Chem. Abstracts (CA106 (1):46295), discloses that 3,4,5,6-tetrafluorophthalic acid may be completely decarboxylated to 1,2,3,4-tetrafluorobenzene. The conditions for complete decarboxylation are in an aqueous medium from 210° to 300° C., with no catalyst. In the presence of a catalyst, which may be metallic copper, zinc, cadmium, iron, cobalt or nickel, or the oxides, hydroxides or carbonates of those metals, the reaction may be run between 100° and 270° C. with the preferred range being 160° to 200° C. Impurities of trifluorophenol and 2,3,4,5-tetrafluorobenzoic acid were also produced.

Japanese Patent Application 86/290399 as abstracted in Chem. Abstracts (CA109 (19) 170038e), discloses that 3,5,6-trifluoro-4-hydroxyphthalic acid may be decarboxylated by heating the compound for three hours, in water, under nitrogen atmosphere, at 140° C. (in a sealed tube) to yield 2,4,5-trifluoro-3-hydroxybenzoic acid.

Japanese Patent JP 1025737 as abstracted in Derwent (Acc. No. 89-073118/10), discloses that polyhalogenated phthalic acids may be decarboxylated to form polyhalogenated benzoic acids by heating the acid at a temperature of 100°-200° C., for 0.5 to 5 hrs., in the presence of a tertiary amine, and optionally in the presence of a nonpolar organic solvent. Further heating under the same conditions converts the polyhalobenzoic acid to a polyhalobenzene. Alternatively, the polyhalophthalic acids may be heated in the presence of the same reagents, at a temperature of 130° to 270° C. to yield polyhalobenzenes directly.

In our laboratories, attempts were made to prepare polyfluorobenzenes and fluorochlorobenzenes by decarboxylating the corresponding corresponding phthalic or benzoic acid. The decarboxylations proved to be difficult. The following table summarizes these experiments.

Decarboxylation of Various 4,5-Fluorophthalic and Fluorobenzoic Acids

| Compound | Conditions | Results |
|---|---|---|
| (1) 2,4,5 Trifluorobenzoic Acid | 130°/80% $H_2SO_4$ | NR |
| (2) 2,3,4,5 Tetrafluorobenzoic Acid | 200-210° Diglyme/ CuO Catalyst | NR |
| (3) 2,3,4,5 Tetrafluorobenzoic Acid | 200-210° Diglyme $Cu_2O$ Catalyst | NR |
| (4) 2,4,5 Trifluorobenzoic Acid | 190°/DMSO | NR |
| (5) 3,4,5,6 Tetrafluorophthalic Acid | 190°/DMSO | Benzoic Acid formed |
| (6) 3,4,5,6 Tetrafluorophthalic Acid | 150° Tri-n-butylamine | NR |
| (7) 3,4,5,6 Tetrafluorophthalic Acid | 160° Triethylamine/ Xylene | NR |
| (8) 3,4,5,6 Tetrafluorophthalic Acid | 160° Tri-n-butylamine/Xylene | NR |

NOTE: NR means No Reaction Observed

SUMMARY OF THE INVENTION

Polyfluorobenzenes are prepared by the decarboxylation of polyfluorophthalic acids or polyfluorobenzoic acids, in the presence of a Cu, CuO or $Cu_2O$ catalyst in either quinoline or N-methyl-2-pyrrolidone as a solvent.

DETAILED DESCRIPTION OF THE INVENTION

Surprisingly it has now found that poly-fluorinated phthalic acids or benzoic acids containing two to four fluorine substituents may be totally decarboxylated by heating in quinoline or n-methyl-2-pyrrolidone in the presence of a catalytic amount of copper or copper salt. The poly-fluorobenzoic acid may optionally include a chlorine substituent ortho to the carboxyl group. As shown in the following equation, the product of the decarboxylation reaction is a poly-fluorobenzene.

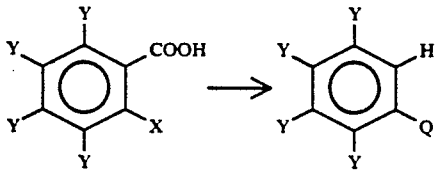

Where X may be COOH or Cl, Q may be H or Cl, and each Y may be independently H or F provided that at least 2 Y's are F Metallic copper, $Cu_2O$, CuO are effective catalysts for the present reaction. However, copper metal provides a slower reaction than either $Cu_2O$ or CuO. Accordingly, the oxides are the preferred catalysts for the reaction. The catalysts are effective when present in amounts greater than about 1% of the weight of the starting material. Catalyst amounts such as 50% of the weight of the starting material, or even higher, may be used. However, the preferred catalyst amount is about 5 to 10% of the weight of the starting material.

Although the exact mechanism is not understood, it has been observed that the presence of air tends to slow the decarboxylation reaction. Therefore, it is preferred to exclude air through the use of an inert atmosphere. For example, the reaction may be run under helium, nitrogen, or argon. Alternatively, the reaction may be run in a mixed solvent containing a lower boiling material which volitalizes and drives out air. Other methods of excluding air are well known to those skilled in the art and any method of excluding air will serve the purposes of this invention.

Quinoline and N-methyl-pyrrolidone are suitable solvents for the reaction of the present invention. Quinoline is the preferred solvent for species in which there is a chlorine ortho to a carboxyl group. The reaction may be run at temperatures between about 170° up to the boiling point of the solvent. Generally the reactions are rather slow at temperatures appreciably below 170° C. On the other hand, at temperatures close to the boiling point of the solvent, the reactions proceed quickly, but side-products are formed. The preferred temperature range for the reaction is between about 190° and 200° C.

It has been observed that phthalic acids decarboxylate more readily than benzoic acid. Although we do not wish to be bound by theory, it is believed that the decarboxylation of phthalic acid occurs sequentially. That is, the phthalic acid first decarboxylates to benzoic acid, and then the benzoic acid decarboxylates further to yield the benzene derivative. The decarboxylation reaction must be conducted carefully to insure that the intermediate benzoic acid derivative is fully decarboxylated.

The reactions may be run at atmospheric or elevated pressures. However, atmospheric pressures are preferred because no specialized equipment is required. Typical reaction times range from 5 to 30 minutes in quinoline and up to 2 hours in N-methyl-2-pyrrolidone. Even longer reactions may be run in some cases. However, many reactions are over with within 10 to 15 minutes at the preferred reaction temperature. The course of the reaction may be followed by gas chromatographic analysis of reaction aliquots. Since $CO_2$ evolves during the reaction, the course of the reaction may also be monitored by observing $CO_2$ evolution from the mixture.

Many of the reaction products are volatile and may be distilled from the reaction mixture as they are formed. Higher boiling products such as 1-chloro-3,4, difluorobenzene may be isolated either by distillation or by extraction after the reaction is complete.

EXAMPLES

EXAMPLE 1

Preparation of 1,2,4-trifluorobenzene from 2,4,5-trifluorobenzoic acid in quinoline After 1.0 g (0.0057 mol) of 2,4,5-trifluorobenzoic acid, 0.11 g of copper (II) oxide and 10 mL of quinoline were placed in a reaction vessel, the contents were heated under a nitrogen atmosphere at 200° C., at which time the reaction started effervescing. After heating at this temperature for 0.5 h, the reaction was cooled, and an internal standard added. $^{19}F$ NMR analysis of the reaction mixture indicated 0.6 g (80%) of 1,2,4-trifluorobenzene was formed.

EXAMPLE 2

Preparation of 1,2,4-trifluorobenzene from 2,4,5 trifluorobenzoic acid in N-Methyl-2-Pyrrolidone (NMP)

After 0.5 g of 2,4,5-trifluorobenzoic acid, 0.1 g of copper (II) oxide and 10 mL of NMP were placed in a reaction vessel, the contents were heated under a nitrogen atmosphere at 150° C., at which time the reaction started effervescing. After heating at this temperature for 3 h, the reaction was cooled, and an internal standard added. $^{19}F$ NMR analysis of the reaction mixture indicated 0.284 g (75%) of 1,2,4-trifluorobenzene was formed.

EXAMPLE 3

Preparation of 1,2,4-trifluorobenzene from 3,4,6-trifluorophthalic acid in quinoline As above, 0.25 g of 3,4,6-trifluorophthalic acid, 0.02 g of copper (II) oxide and 5 mL of quinoline were combined and heated to 190° C. for 2 h. After cooling, an internal standard was added. $^{19}F$ NMR analysis of the reaction mixture indicated 0.07 g (44%) of 1,2,4-trifluorobenzene was formed.

EXAMPLE 4

Preparation of 1,2,3,4-tetrafluorobenzene from 3,4,5,6-tetrafluorophthalic acid in quinoline Using the procedure above, 1.0 g of 3,4,5,6-tetrafluorophthalic acid, 0.11 g of copper (II) oxide and 10 mL of quinoline were combined and heated to 60° C. under an atmosphere of nitrogen for 0.55 h. Addition of a suitable internal standard followed by $^{19}F$ NMR analysis indicated formation of 0.49 g (78%) of 1,2,3,4-tetrafluorobenzene.

EXAMPLE 5

Preparation of 1,2,3,4-tetrafluorobenzene from 3,4,5,6-tetrafluorophthalic acid in N-Methyl-2-Pyrrolidone (NMP)

Using the procedure above, 0.5 g of 3,4,5,6-tetrafluorophthalic acid, 0.1 g of copper (II) oxide and 10 mL of NMP were combined and heated to 150° C. under an atmosphere of nitrogen for 2 h. Addition of a suitable internal standard followed by $^{19}F$ NMR analysis indicated formation of 0.16 g (51%) of 1,2,3,4-tetrafluorobenzene.

EXAMPLE 6

Preparation of 1,2,3,4-tetrafluorobenzene from 3,4,5,6-tetrafluorobenzoic acid in quinoline Using the procedure above, 0.25 g of 2,3,4,5-tetrafluorobenzoic acid, 0.02 g of copper (II) oxide and 5 mL of quinoline were combined and heated to 190° C. under an atmosphere of nitrogen for 2 h. Addition of a suitable internal standard followed by 19F NMR analysis indicated formation of 0.138 g (67%) of 1,2,3,4-tetrafluorobenzene.

EXAMPLE 7

Preparation of 1,4-difluorobenzene from 3,6-difluorophthalic anhydride in quinoline Using the procedure above, 0.23 g of 3,6-difluorophthalic anhydride, 0.023 g of copper (II) oxide and 3 mL of quinoline were combined and heated to 180° C. GCMS analysis of the reaction mixture indicated complete consumption of the starting material and formation of 1,4-difluorobenzene as the major product. A small amount of 2,2',5,5'-tetrafluorobiphenyl was formed as a by-product.

EXAMPLE 8

Preparation of 1,4-difluorobenzene from 3,6-difluorophthalic anhydride in N-Methyl 2-Pyrrolidone (NMP)

Using the procedure above, 0.5 g of 3,6-difluorophthalic anhydride, 0.1 g of copper (II) oxide and 10 mL of NMP were combined and heated to 150° C. for 12 h. GCMS analysis of the reaction mixture indicated complete consumption of the starting material and formation of 1,4-difluorobenzene as the major product. A small amount of 2,2',5,5'-tetrafluorobiphenyl was formed as a by-product.

EXAMPLE 9

Preparation of 1-chloro-3,4-difluorobenzene from 2-chloro-4,-difluorobenzoic acid in quinoline Using the procedure above, 0.5 g of 2-chloro-4,5-difluorobenzoic acid, 0.1 g of copper (II) oxide and 10 mL of quinoline were heated to 190° C. for 0.5 h. GCMS analysis of the reaction mixture indicated formation of 1-chloro-3,4-difluorobenzene.

We claim:

1. A process for the production of polyfluorobenzenes represented by the following formula:

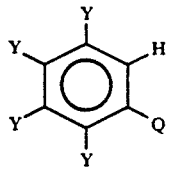

wherein Q may be H or Cl, and each Y maybe be independently F or H provided that at least 2 Y's are F which comprises heating a polyfluorobenzoic acid or polyfluorophthalic acid starting material represented by the following formula:

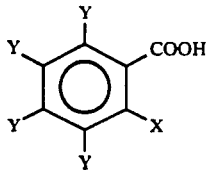

wherein X may be COOH or Cl, and each Y maybe be independently F or H provided that at least 2 Y's are F in a solvent selected from the group consisting of quinoline and n-methyl-2-pyrrolidone, in the presence of a catalyst selected from the group consisting of copper metal, $Cu_2O$ and CuO.

2. A process according to claim 1 wherein Q is H and X is COOH.

3. A process according to claim 1 wherein Q and X are Cl.

4. A process according to claim 1 wherein Q is H and X is three Y's are F and one Y is H.

5. A process according to claim 1 wherein Q and X are Cl and three Y's are F and one Y is H.

6. A process according to claim 1 wherein Q is H and X is COOH and two Y's are F and two Y's are H.

7. A process according to claim 1 wherein Q and X are Cl and two Y's are F and two Y's are H.

8. A process according to claim 1 for the production of 1,2,4-trifluorobenzene wherein the starting material is 3,4,6-trifluorophthalic acid.

9. A process according to claim 1 for the production of 1,2,4-trifluorobenzene wherein the starting material is 2,3,5-trifluorobenzoic acid.

10. A process according to claim 1 for the production of 1,2,3,4-tetrafluorobenzene wherein the starting material is 3,4,5,6-tetrafluorophthalic acid.

11. A process according to claim 1 for the production of 1,2,3,4-tetrafluorobenzene wherein the starting material is 2,3,4,5-tetrafluorobenzoic acid.

12. A process according to claim 1 for the production of 1-chloro-3,4-difluorobenzene wherein the starting material is 2-chloro-4,5-difluorobenzoic acid.

13. A process according to claim 1 for the production of 1,4-difluorobenzene wherein the starting material is 3,6-difluorophthalic acid.

14. A process according to claim 1 for the production of 1,4-difluorobenzene wherein the starting material is 2,5-difluorobenzoic acid.

* * * * *